United States Patent [19]
Takamura et al.

[11] Patent Number: 5,810,714
[45] Date of Patent: Sep. 22, 1998

[54] ENDOSCOPIC APPARATUS FOR REDUCING UNWANTED NOISE RADIATED FROM AN ELECTRONIC ENDOSCOPE

[75] Inventors: Koji Takamura, Hachioji; Nariaki Saito, Hino; Seiji Iwasaki, Tsukui-gun; Koji Yamaya, Hachioji; Jun Hiroya, Tokyo, all of Japan

[73] Assignee: Olympus Optical Co., Ltd., Tokyo, Japan

[21] Appl. No.: 579,266

[22] Filed: Dec. 27, 1995

[30] Foreign Application Priority Data

Apr. 25, 1995 [JP] Japan .................................. H7-101337
Aug. 2, 1995 [JP] Japan .................................. H7-197718

[51] Int. Cl.⁶ .................................................. A61B 1/04
[52] U.S. Cl. ........................................ 600/134; 600/130
[58] Field of Search ................................ 600/134, 132, 600/130, 118, 112, 110, 109; 348/65, 76, 75, 74

[56] References Cited

U.S. PATENT DOCUMENTS

| | | | |
|---|---|---|---|
| 4,607,621 | 8/1986 | Wheeler | 600/110 |
| 4,919,114 | 4/1990 | Miyazaki | 600/110 |
| 4,998,182 | 3/1991 | Krauter et al. | 600/110 X |
| 5,170,775 | 12/1992 | Tagami | 600/134 X |
| 5,271,381 | 12/1993 | Ailinger et al. | 600/128 |
| 5,569,158 | 10/1996 | Suzuki et al. | 600/110 |

FOREIGN PATENT DOCUMENTS

| | | |
|---|---|---|
| 3431 994 A1 | 4/1985 | Germany . |
| 3600 283 A1 | 7/1986 | Germany . |
| 3627 327 A1 | 2/1987 | Germany . |
| 4-183432 | 6/1992 | Japan . |
| 2 148 661 | 5/1985 | United Kingdom . |

Primary Examiner—Richard J. Apley
Assistant Examiner—John Leubecker
Attorney, Agent, or Firm—Armstrong, Westerman Hattori, McLeland & Naughton

[57] ABSTRACT

An endoscopic apparatus comprising a solid-state image pickup device installed in an insert assembly, a signal transmission member for conducting the electric signal into which the solid-state image pickup device photoelectrically converts an optical image, and a flexible tube-like metal member that makes up part of the cover of the insert assembly and/or a flexible tube-like metal member that constitutes part of the universal cord, whereby the signal transmission member is inserted through the insert assembly member and the universal cord, the shield member that covers the signal transmission member is disposed at least in part of the insert assembly and/or part of the universal cord assembly, and the shield member and the metal members are set to be equipotential to each other.

21 Claims, 14 Drawing Sheets

ENDOSCOPIC APPARATUS FOR REDUCING UNWANTED NOISE RADIATED FROM AN ELECTRONIC ENDOSCOPE

BACKGROUND OF THE INVENTION

1. Field of the Invention:

The present invention relates to an endoscopic apparatus that reduces unwanted noise radiated from an electronic endoscope.

2. Related Art Statement:

Endoscopes now in widespread use allow an operator to observe a lesion in the body cavity by inserting an elongated insert assembly into the body cavity, and, if necessary, to treat and cure the lesion by passing a treatment instrument through an instrument guide channel of the endoscope.

Among these endoscopes, some are electronic endoscopes that employ a solid-state image pickup device such as a charge coupled device (CCD) as the image pickup means.

In these electronic endoscopes, an optical image of a subject to be observed is formed on an imaging surface through an objective optical system, the optical image formed on the imaging surface is photoelectrically converted into an electric signal, and the electric signal is sent to signal processing means via electric signal transmission means.

The signal processing means produces a video signal based on the electric signal, and the video signal is then sent to a monitor apparatus, where the optical image of the subject is provided on screen to be observed.

The electric signal a signal cable conducts from the solid-state image pickup device to a video processor is a high-frequency signal. Therefore, the signal cable that conducts the electric signal is likely to radiate noise. The endoscope is constructed by assembling a number of metal members, each having conductive characteristics, a complicated structure, and the signal cable and light into guide are housed in these numerous metal members.

In the design of the endoscope, no consideration is given to the mounting layout of metal members built-in, and priority is given to the regularity of the structure of the endoscope in view of increasing ease of assembly during assembling. Thus, after the endoscope is assembled, the signal cable is likely to suffer from detachment of its metal member which work as a cover, thereby causing the noise radiation level to increase.

Signal lines are separately connected to their respective circuit grounds, while metal members which make up a cover have no distinct electric continuity means after assembly. This causes the noise radiation level to increase.

Japanese Patent Application Laid-open No. Hei-4-183432 has disclosed an electronic endoscope, in which unwanted noise reduction members such as ferrite cores are provided to noise sources to prevent unwanted noise radiation.

Since the electronic endoscope disclosed by the above cited Japanese Patent Application Laid-open No. Hei-4-183432, however, requires that an unwanted radiated noise reduction member be installed to each noise radiating line on a line-by-line basis, a substantial cost increase results and additional mounting space for unwanted radiated noise reduction members is required as well. Space requirement is thus increased, leading to a bulky design of the endoscope. For this reason, the number of unwanted radiated noise reduction members in use should be limited.

Since the endoscopic apparatus having an electronic endoscope handles a diversity of signals whose levels are different from those of ordinary electric signals, it is desired to suppress unwanted noise radiated from the electronic endoscope as much as possible, namely, it is desired to fully implement EMI (Electromagnetic Interference) preventing steps in electronic apparatuses.

In one of the conventionally available noise suppressing methods for grounding unwanted radiated noise from the signal cable to ground, metal members of the insert assembly, the operation assembly, and the universal cord in the electronic endoscope are put into surface contact with each other and secured with screws to assure electric connection or continuity and to make the entire endoscope a conductive path. In this case, however, the contact area in surface contact is often insufficient, with continuity opened, or the threaded portion of a fixing screw that binds metal members suffers variations in contact, opening electric continuity. When an adhesive agent is used to connect members, an adhesive layer works as an isolation film causing non-continuity therebetween. When metal members are spaced apart, a non-continuity portion is created, resulting in a stray capacity and possibly radiating unwanted noise.

OBJECTS AND SUMMARY OF THE INVENTION

It is an object of the present invention to provide an endoscopic apparatus that reduces unwanted radiated noise from an electronic endoscope having a solid-state image pickup device.

It is another object of the present invention to provide an endoscopic apparatus that reduces noise ingress from the outside.

It is yet another object of the present invention to provide an electronic endoscope, wherein metal members from the front end portion of an insert assembly over to a connector assembly are electrically connected in an assured manner to reduce radiated noise level.

The endoscopic apparatus according to the present invention comprises a solid-state image pickup device installed in an insert assembly, a signal transmission member for conducting the electric signal into which the solid-state image pickup device photoelectrically converts an optical image, and a flexible tube-like metal member that makes up part of the cover of the insert assembly and/or a flexible tube-like metal member that makes up part of the universal cord, whereby the signal transmission member is inserted through the insert assembly member and the universal cord, the shield member that covers the signal transmission member is disposed at least in part of the insert assembly and/or part of the universal cord assembly, and the shield member and the metal members are equipotential to each other.

BRIEF DESCRIPTION OF THE DRAWINGS

FIG. 1 is an explanatory view showing generally the construction of the endoscopic apparatus.

FIG. 2 is a wiring diagram showing electromagnetic interference preventing means of a signal cable.

FIG. 3 is a cross-sectional view taken along line I—I in FIG. 1.

FIG. 4 is a cross-sectional view taken along line II—II in FIG. 1.

FIG. 5 is a cross-sectional view taken along line III—III in FIG. 1.

FIG. 6 is a cross-sectional view showing the construction of the front end portion of the insert assembly.

FIG. 7 is a cross-sectional view taken along line IV—IV in FIG. 6.

FIG. 8 is a cross-sectional view showing the construction of the front end portion of the insert assembly.

FIG. 9 is a cross-sectional view taken in FIG. 8 in the same line as FIG. 7 is taken along the IV—IV line in FIG. 6.

FIG. 11 is a cross-sectional view showing the connection between an operation assembly support plate and an angle shaft.

FIG. 12 is an explanatory view showing the location of adhesive agent application on the screw.

FIG. 13 shows the connection between an air/water control section and the operation assembly support plate.

FIG. 14 is a cross-sectional view showing the prior art connection method of the switch section to the operation assembly.

FIG. 15 is a cross-sectional view showing the connection method of the switch section to the operation assembly.

FIG. 16 is a cross-sectional view showing the connection of the switch section of different material to the operation assembly.

FIG. 17 is a cross-sectional view showing generally the construction of the front end portion.

FIG. 18 is a cross-sectional view taken along line V—V in FIG. 17.

FIG. 19 is an explanatory view showing the connection portion between a back block and a first bending portion joint segment.

FIG. 20 shows a poor connection state in the connection portion.

FIG. 21 is a view looked from the arrow F in FIG. 20.

FIG. 22 shows the action of the connection portion poorly connected.

FIG. 23 is a cross-sectional view showing a good connection state wherein the first bending portion joint segment is secured to the back block using a screw.

FIG. 24 shows a dimensional setting of the back block and the first bending portion joint segment.

FIG. 25 shows the function of the fixing screw that secures the first bending portion joint segment to the back block.

FIG. 26 shows the first bending portion joint segment that is connected to the back block.

FIG. 27 shows the instrument port ring and its vicinity.

FIG. 28 is an explanatory view showing the insulating film that is being peeled off the metal member.

FIG. 29 is a cross-sectional view showing the metal member with its insulating film peeled off.

FIG. 30 is an explanatory view showing the connection state.

DETAILED DESCRIPTION OF THE PREFERRED EMBODIMENTS

Figure 1:
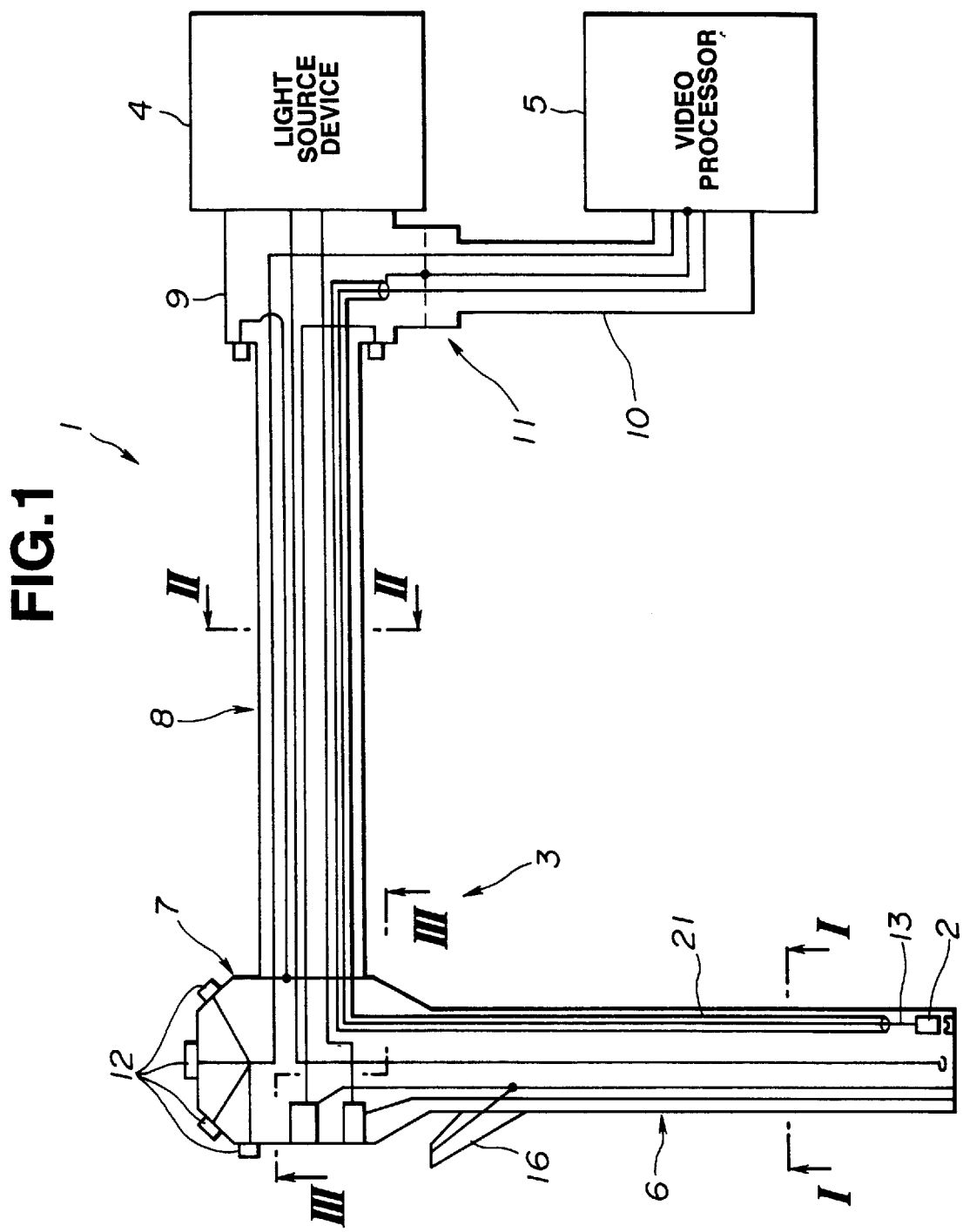
FIGS. 1 through 5 show a first embodiment of the present invention.

Referring now to the drawings, the embodiments of the present invention are now discussed.

The first embodiment of the present invention is discussed referring to FIGS. 1 through 5.

As shown in FIG. 1, an endoscopic apparatus 1 comprises an electronic endoscope 3 having a built-in solid-state image pickup device 2, a light source device 4 for feeding illumination light to the electronic endoscope 3, and a video processor 5 for driving the solid-state image pickup device 2 in the electronic endoscope and processing signals output by the solid-state image pickup device 2. Designated 16 is an instrument port to be described later.

The electronic endoscope 3 has an elongate insert assembly 6 that is flexible, and a large-diameter operation assembly 7 that is continuous to and proximal to the insert assembly 6. A flexible universal cable 8 extends from one side of the operation assembly 7, and disposed on the end of the universal cable 8 is a scope connector assembly 9 that works as the connection fitting detachably mounted to the light source device 4. Disposed on a side of the scope connector assembly 9 is an electric connector 11 that works as the connection fitting for the interconnect cable 10 to be connected to the video processor 5. The operation assembly 7 is provided with a switch section 12 that controls the video processor 5, for example, to freeze an endoscopic image presented on a monitor screen.

The signal cable 13 that extends from the solid-state image pickup device 2 built in inside the front end portion of the insert assembly 6 of the electronic endoscope 3 is passed through the insert assembly 6, operation assembly 7, and universal cord 8 and is connected to the electric connector 11 on the scope connector assembly 9. The signal cable 13 is covered over its total length with a first shield 21 as electromagnetic interference preventing means for enhancing shield effect.

Each cover of the insert assembly 6, operation assembly 7, switch section 12, universal cord 8 and electric connector 11 in the electronic endoscope is constructed of a metal member having conductivity or a member coated with a conductive metal film.

The connection fitting between the insert assembly 6 and the operation assembly 7, the connection fitting between the operation assembly 7 and the switch section 12, the connection fitting between the switch section 12 and the universal cord 8, and the connection fitting between the universal cord 8 and the electric connector 11 have a structure in which electric continuity is assured by keeping in contact one conductive surface with another. Thus, the components contained in the electronic endoscope 3 is enclosed by the metal members that are equipotentially connected.

Figure 2:
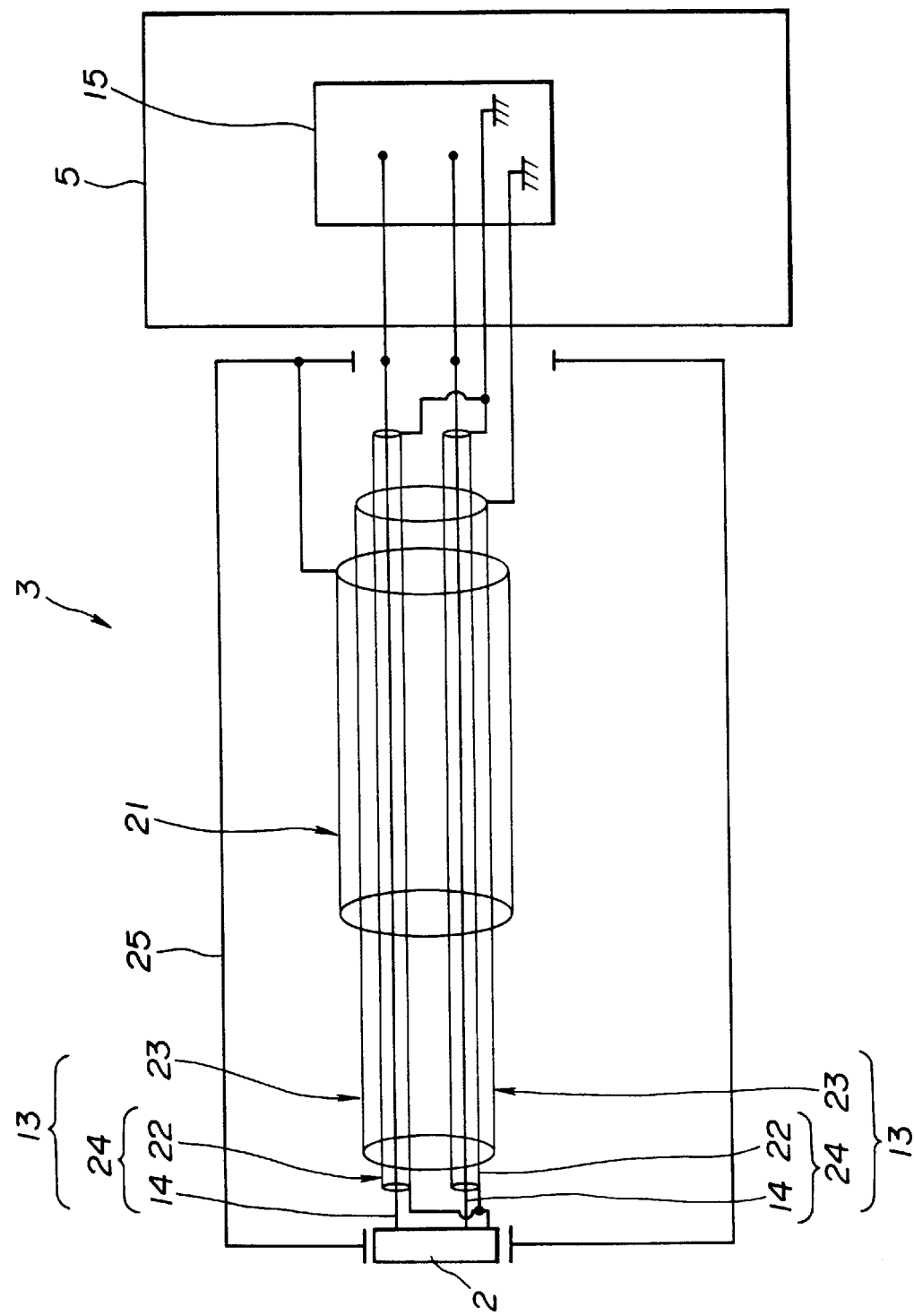

As shown in FIG. 2, the electric signal into which the solid-state image pickup device 2 photoelectrically converts an image is transmitted through conductors 14 in the signal cable and is coupled with a circuit board 15 disposed in the video processor 5.

The signal cable 13 that conducts the electric signals output by the solid-state image pickup device 2 is made up of a plurality of conductors 14 and the conductors 14 carry electric signals of a diversity of driving frequencies. For this reason, signals are likely to mutually interfere with each other (hereinafter referred to as interference noise), and thus a second shield 22 is disposed to cover each conductor 14 to form a coaxial cable 24 to avoid noise interference. Namely, the conductor 14 and the shield 22 make up the coaxial cable 24, and the signal cable 13 is thus made up of a plurality of coaxial cables 24.

Although each coaxial cable 24 that makes up the signal cable 13 is shielded by the second shield 22, noise is still likely to leak out of the coaxial cable 24, and thus the plurality of coaxial cables 24 are covered with a third shield 23. Both the second shield 22 and the third shield 23 are connected to the ground on the circuit board 15.

To suppress unwanted radiated noise such as the one which the second shield 22 and third shield 23 are unable to suppress to a satisfactory level, for example, noise due to static coupling arising from the voltage difference between signal lines or noise due to electromagnetic induction arising from signal currents, the first shield 21 is used as the outermost covering for the signal cable 13, and further the first shield 21 is connected to the scope conductive covering member 25 such as a scope metal covering (hereinafter referred to as metal covering member) that constitutes the electronic endoscope 2.

The first shield 21 is isolated from the conductors 14, the second shields 22 and the third shield 23 to assure the safety of a patient particularly during high-frequency treatment. The first shield 21 is, for example, a metal braided shield of a density of 50% or more, and which may be wrapped on the signal cable 13 in a multi-layered fashion to the extent that the contents of the endoscope allow further filling of the endoscope.

Figure 3:
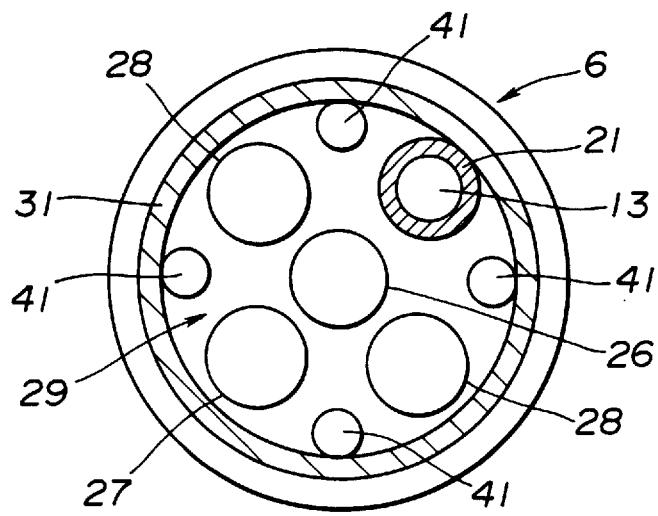

As shown in FIG. 3, the insert assembly 6 of the electronic endoscope 2 accommodates inside a light guide 26, the signal cable 13, a suction tube 27, air/water feed tubes 28 and the like. To provide the insert assembly 6 with an inner space 29 that allows the content of the insert assembly 6 to pass therethrough, the insert assembly 6 has, as its inner most layer, an insert assembly metal member 31 that serves as a framing structure of the insert assembly 6 while at the same time serving as metal covering of the insert assembly 6. To reduce noise arising from potential difference, the first shield 21 that covers the signal cable 13 is arranged in a position that is in contact with or in close vicinity of the insert assembly metal member 31. A reference numeral 41 designates an angle wire to allow the bending portion of the endoscope to bend to look leftward or downward and upward or downward.

Figure 4:
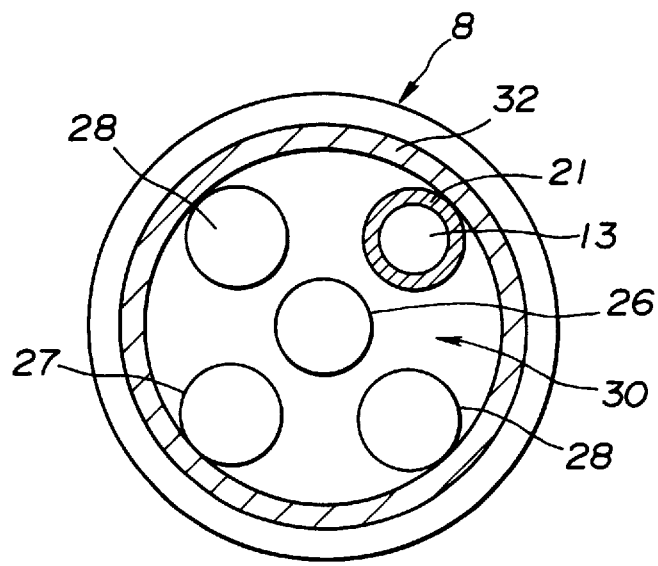

As shown in FIG. 4, in almost the same way as in the insert assembly 6, the light guide 26, the signal cable 13, the suction tube 27, the air/water feed tubes 28 and the like are arranged inside the universal cord 8. To provide the universal cord 8 with an inner space 30 that allows the content of the universal cord 8 to pass therethrough, the universal cord 8 has, as its inner most layer, a universal cord metal member 32 that serves as a framing structure of the universal cord 8 while at the same time serving as metal covering of the universal cord 8. To reduce noise arising from potential difference, the first shield 21 that covers the signal cable 13 is arranged in a position that is in contact with or in close vicinity of the universal cord metal member 32.

Figure 5:
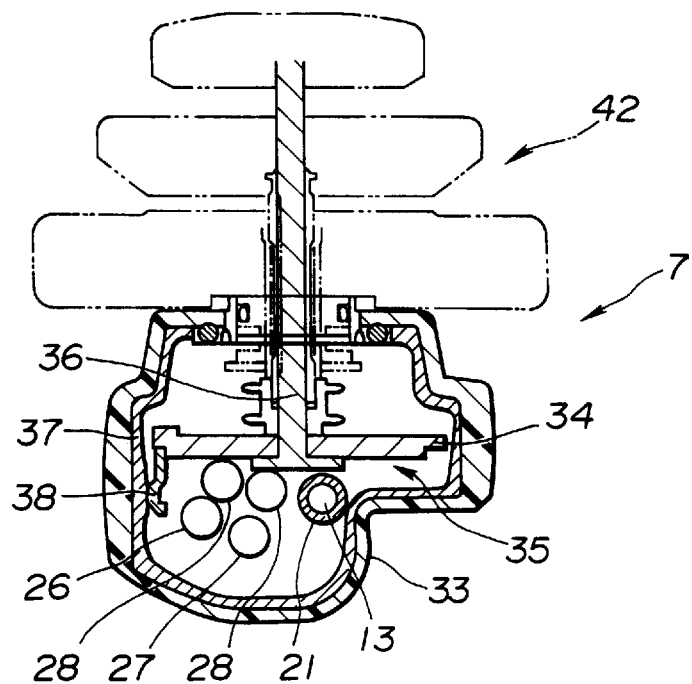

Furthermore, as shown in FIG. 5, the light guide 26, the signal cable 13, the suction tube 27, the air/water feed tubes 28 and the like are accommodated in a space 35 that is formed by an operation assembly resin casing 33 of the operation assembly 7 and an operation assembly support metal plate 34 for the operation assembly 7.

The operation assembly 7 is provided with an angle control section 42 made up of a plurality of angle knobs shown by alternate long and two short dashes line to allow the unshown bending portion attached at the end of the insert assembly 7 to curve to look toward the left and right or up and down directions. As its support, the angle control section 42 has an angle shaft 36 that makes up a conductive covering 25 for the operation assembly 7, and the angle shaft 36 is supported by the operation assembly support plate 34.

The operation assembly resin casing 33 of the operation assembly 7 has as its inner surface a conductive coating, and thus the entire inner surface of the operation assembly 7 is formed of the conductive coating 37 that works as the conductive covering 25 for the operation assembly 7. Since an elastic pressure member 38 disposed on the side of the operation assembly support plate 34 keeps the conductive coating 37 in contact with the operation assembly support plate 34, the operation assembly support plate 34 as the metal member of the operation assembly 7, the angle shaft 36 and the conductive coating 37 remain equipotential.

To reduce noise arising from potential difference in the operation assembly 7 as well, the first shield 21 covering the signal cable 13 is disposed in a position in contact with or in close vicinity of the operation assembly support plate 34, the conductive coating 37 or the angle shaft 36.

Also in the components other than the insert assembly 6, the operation assembly 7 and the universal cord 8, the first shield 21 covering the signal cable 13 is disposed in a position in contact with or in close vicinity of a metal member or a substantially metal member that is formed of metal covering such as conductive coating.

To form the electromagnetic interference preventing means, the first shield that covers the signal cable over its total length is disposed in contact with or in close vicinity of conductive coverings that are formed of equipotentially connected metal members and conductive coatings in the components that make up the electronic endoscope, such as the insert assembly, the operation assembly and the universal cord. When the endoscope is used to investigate or treat the subject, part of the first shield is set to be equipotential with metal members as the conductive covering members of the insert assembly, the operation assembly and the universal cord in the electronic endoscope. Thus, noise arising from potential difference is reduced.

The second shield and the third shield, both covering the signal cable, are connected to circuit grounds, which ground noise picked up by the second shield and third shield, and thus the signal system of the apparatus is free from adverse effect.

Figure 6:
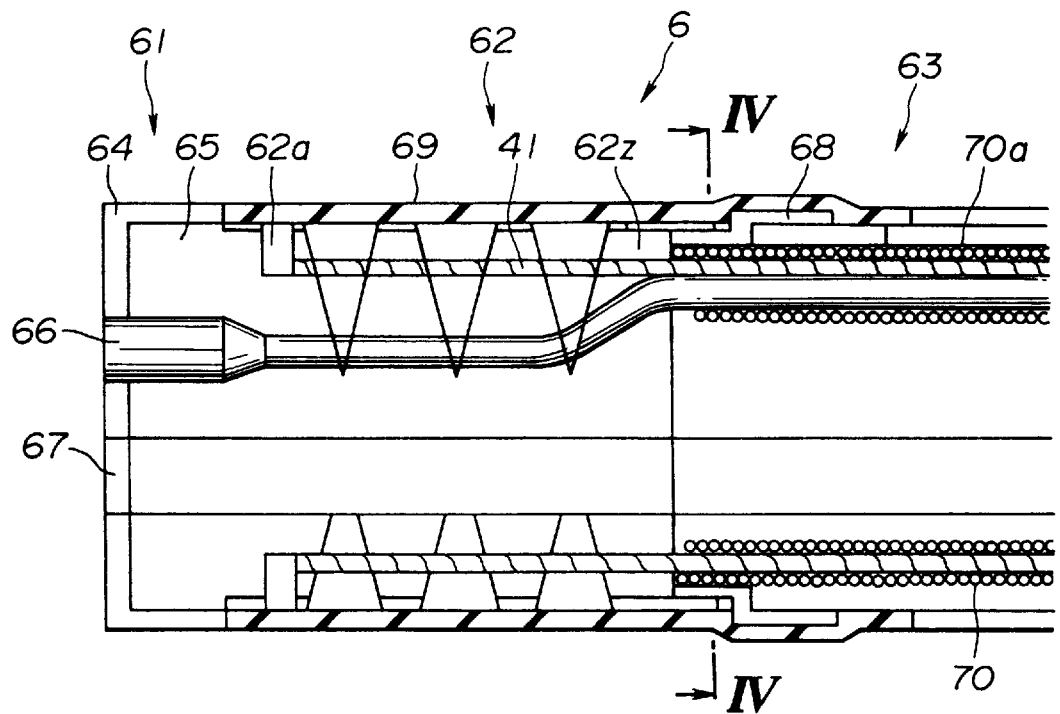
FIGS. 6 and 7 show a second embodiment of the present invention.
Figure 7:
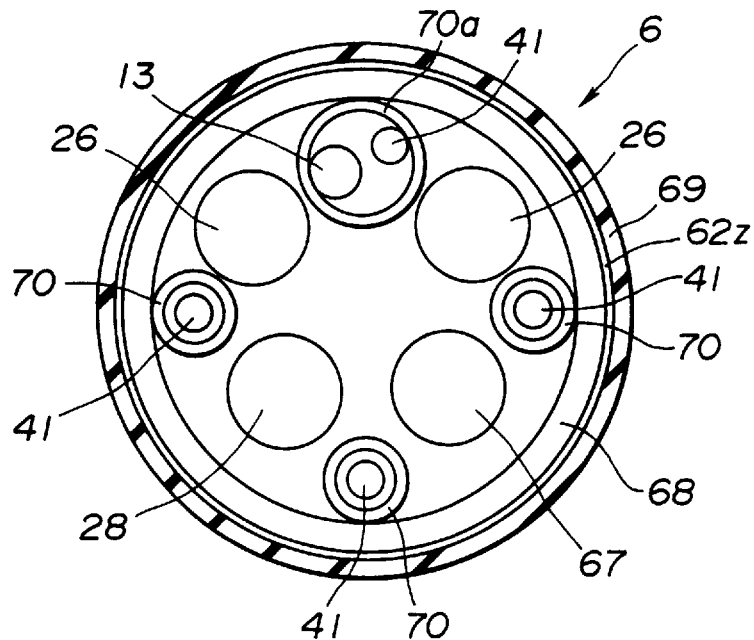

Referring to FIGS. 6 and 7, the second embodiment of the present invention is now discussed.

As shown in FIG. 6, the insert assembly 6 of the electronic endoscope 3 in this embodiment is constructed of an front end portion 61, a bending portion 62, and a flexible portion 63, all of which are integrally connected. The front end portion 61 is made of a front block 64 and a back block 65, and is machined so that it may accommodate an image pickup unit 66 and an instrument passage channel 67. A first bending portion joint segment 62a that makes up the bending portion 62 is fitted into the back block 65 that makes up the front end portion 61. On the other hand, the last bending portion joint segment 62z that also makes up the bending portion 62 is fitted into the bending portion fixing ring 68 of the flexible portion 63. The back end of the front end portion 61, the total length of the bending portion 62 and part of the front end of the flexible portion 63 are covered with a bending portion covering member 69 having elasticity.

An angle wire 41 is connected to the first bending portion joint segment 62a to curve the bending portion 62 which is connected to direct the front end portion 61 to a desired direction. A plurality of angle wires 41 may be disposed to direct the end face of the endoscope upward or downward, or leftward or rightward. The flexible portion 63 through which the angle wire 41 passes has an angle coil pipe 70 that allows the angle wire 41 to pass therethrough without giving adverse effect arising from friction to the flexible portion 63. The angle coil pipe 70 and the angle wire 41 are constructed of conductive materials.

As shown in FIG. 7, the front end of the angle coil pipe 70 is firmly attached to an arbitrary position of the inner circumference of the bending portion fixing ring 68 by means of solder or the like, and the angle coil is arranged so that its interference with the light guide 9, the air/water feed tubes 28, and the instrument passage channel 67 may be avoided. The other end of the angle coil pipe 70 is electrically connected to the operation assembly support plate 34 of the operation assembly 7 and the like.

The signal cable 13 that conducts electric signals is extended from the image pickup unit 66, and the signal cable 13 is routed together with an angle wire 41 through one of the angle coil pipe 70. Thus, this angle coil pipe 70a that allows the signal cable 13 and the angle wire 41 to run together therethrough is greater in diameter than the other angle coil pipes 70. The signal cable 13 may be one or a plurality of cables depending on the specification of the solid-state image pickup device in the image pickup unit 66. In the embodiment, it is assumed that the signal cable 13 is a single cable. The rest of the construction of this embodiment remains unchanged from that of the preceding embodiment, and components similar to those with reference to the preceding embodiment are designated with the same reference numerals, and the explanation on them is not repeated.

As described above, by allowing the signal cable to run through the angle coil pipe made of the conductive metal material, noise radiated from the signal cable is reduced because noise from the signal cable is grounded via the angle coil pipe. The rest of the operation and advantage is identical to that of the preceding embodiment.

Figure 8:
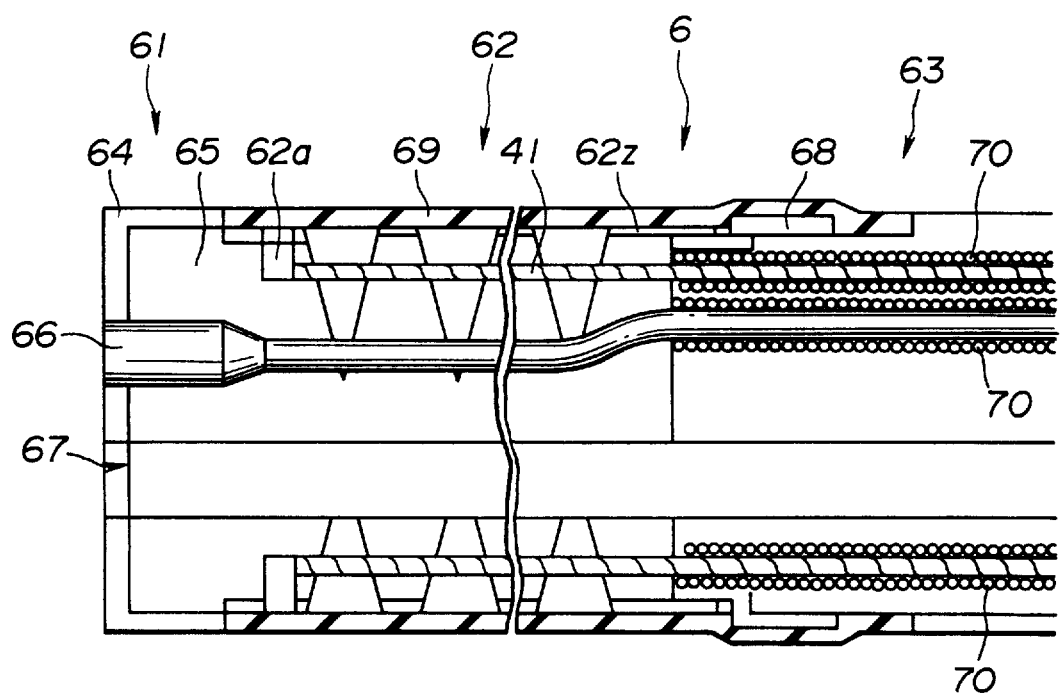
FIGS. 8 and 9 show an alternate example of the second embodiment of the present invention.
Figure 9:
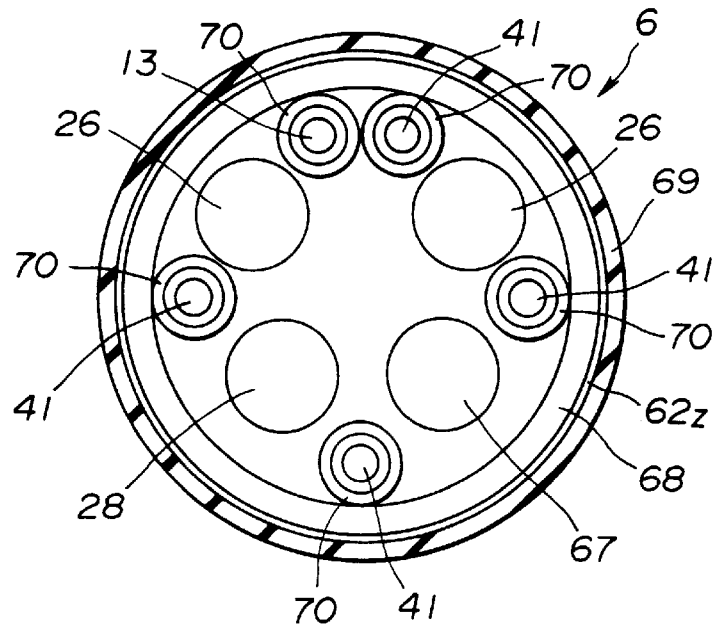

In FIGS. 8 and 9, one angle coil pipe 70 that allows the angle wire 41 to pass therethrough and another angle coil pipe 70 that allows the signal cable 13 to pass therethrough may be separately run. Each of the angle coils 70 is securely attached to an arbitrary position of the inner circumference of the bending portion fixing ring 68 by means of solder or the like as shown in FIGS. 6 and 7. This arrangement accommodates an increased number of the signal cables 13 and angle wires 41.

Figure 10:
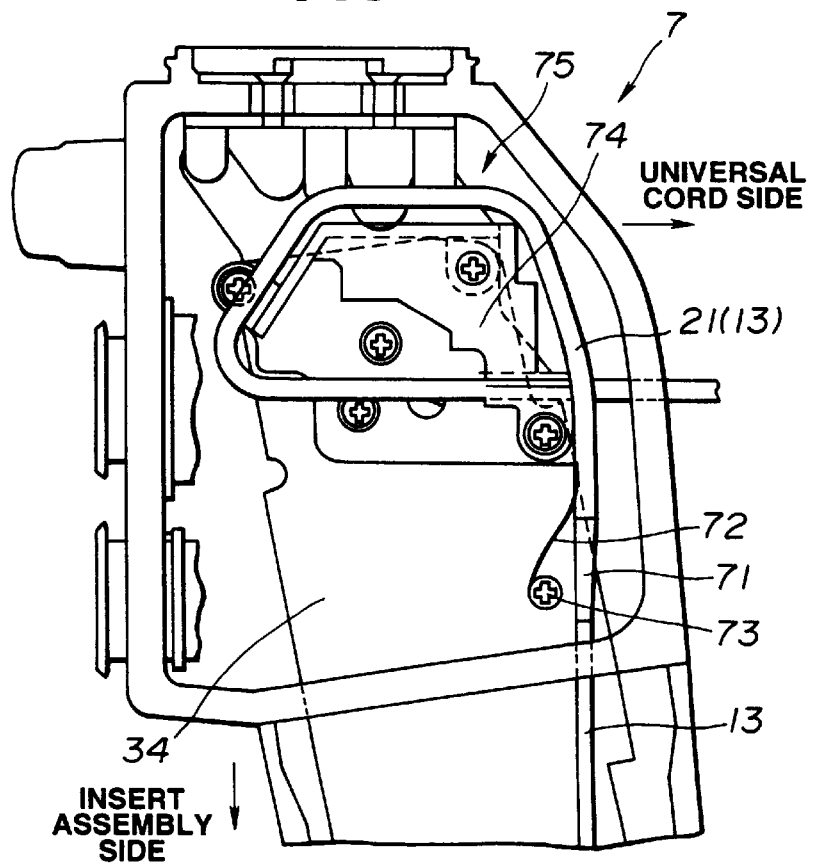
FIG. 10 is an explanatory view showing the signal cable routed in the operation assembly according to a third embodiment of the present invention.

Referring to FIG. 10, the third embodiment of the present invention is now discussed.

As shown, the insert assembly 6 and the universal cord 8 are electrically connected to the operation assembly support plate 34 in the operation assembly 7 in this embodiment. The operation assembly support plate 34 is electrically conductive, and is of a larger and robuster design than the other components because a diversity of components that make up the electronic endoscope are mounted on the operation assembly support plate 34. As a result, the operation assembly support plate 34 forms a grounding. The bulky size of the operation assembly support plate 34 is equivalent to an earth ground.

The signal cable 13 that runs through the electronic endoscope is covered with the first shield 21, as electromagnetic interference preventing means, over its total length of or a part of the signal cable 13 from which a great deal of noise is emitted. Inside the operation assembly the signal cable 13 is likely to emit a great deal of noise and is covered with the first shield 21. In this case, a heat shrinking tube 71 is placed on the first shield 21 at its front end. When placing the heat shrinking tube 71, one end of a jumper wire 72 is soldered to the end of the first shield 21, and the other end of the jumper wire 72 is secured to the operation assembly support plate 34 with a screw 73, so that the first shield 21 and the operation assembly support plate 34 remain equipotential.

When pulled from the insert assembly side or from the universal cord side, the signal cable 13 that is covered with the first shield 21 may suffer a break due to the pull. To avoid such a break, the signal cable 13 is coiled into a cable loop portion 75 that is wrapped around a fixing member 74 attached to the operation assembly support plate 34 to tie the signal cable 13. The rest of the construction of the embodiment remains unchanged from the preceding embodiment, and components equivalent to those with reference to the preceding embodiment are designated with the same reference numerals, and the explanation on them will not be repeated.

Since the first shield covering the signal cable is electrically connected to and thus set be equipotential with the operation assembly support plate in the form of electromagnetic interference preventing means, the level of noise radiated from the signal cable is reduced. Furthermore, the operation assembly support plate to which the first shield covering the signal cable is connected is a metal member having a large capacitance, and the operation assembly support plate is charged by noise conducted by the signal cable, contributing to the reduction of radiated noise level. The rest of the operation and advantage of this embodiment is identical to that of the preceding embodiment.

Figure 11:
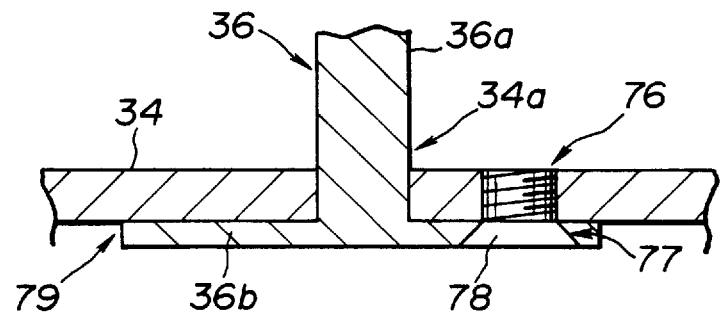
FIGS. 11 through 13 show the connection method to assure electric continuity in the operation assembly.
Figure 12:
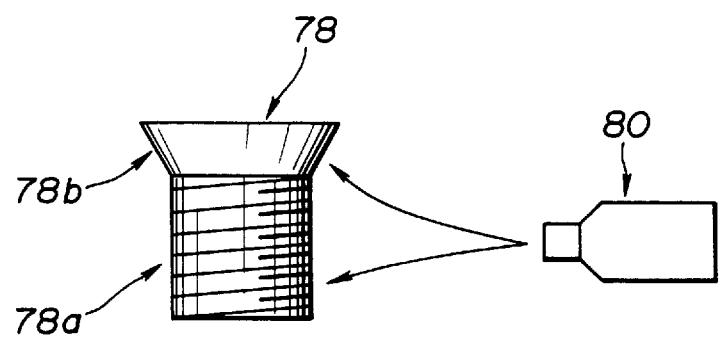
Figure 13:
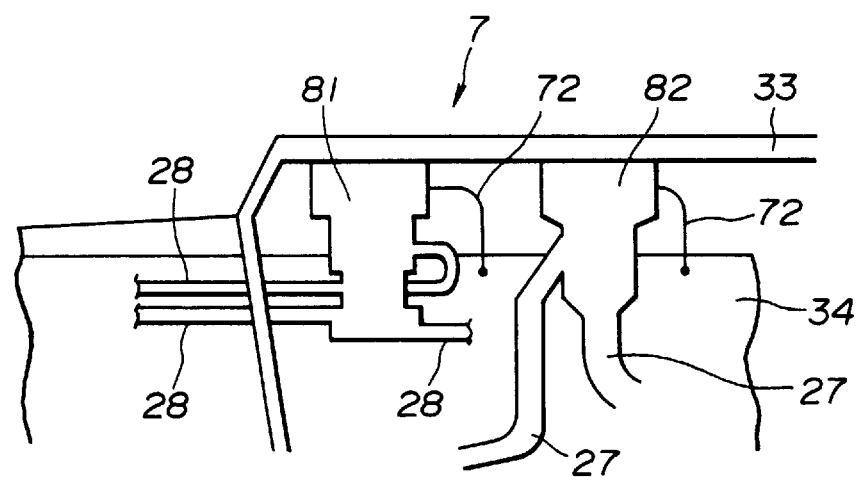

Discussed next referring to FIGS. 11 through 13 is the connection method that achieves firm electric connection in the operation assembly 7.

In this embodiment as shown in FIG. 11, to attach the angle shaft 36 to the operation assembly support plate 34, the shaft portion 36a of the angle shaft 36 is inserted into an axis hole 34a formed in the operation assembly support plate 34, a screw hole or threaded hole 76 formed in the operation assembly support plate 34 is aligned with a screw-head socket 77 formed in the angle shaft 36, and a screw 78 is screwed in to tightly secure the angle shaft 36 to the operation assembly support plate 34. In this case, the top surface of the flange portion 36b of the angle shaft 36 and the bottom surface of the operation assembly support plate 34 form interfaces 79, and to increase tightness of these interfaces 79, the top surface of the flange portion 36b and the bottom surface of the operation assembly support plate 34 are smoothly finished. This arrangement achieves reliable contact surfaces between the operation assembly support plate and the angle shaft and offers assured electric connection therebetween.

As shown in FIG. 12, as a preliminary step before tightening the screw 78, a conductive adhesive 80 is applied to the threaded portion 78a of the screw 78 and the entire circumference of the head side 78b, and then by tightening the screw 78, the angle shaft 36 is rigidly attached to the operation assembly support plate 34. In this way, the conductive adhesive that has been applied to the screw ingresses between the screw and the threaded hole and between the screw and the screw-head socket, enhancing tightness more and assuring electrical connection more.

As shown in FIG. 13, an air/water feed cylinder 81 forming an air/water feed control section and a suction cylinder 82 forming a suction control section in the operation assembly 7 are electrically connected to the operation assembly support plate 34 via respective jumper wires 72. This arrangement assures that the metal members spaced part are electrically connected via the jumper wires.

Figure 14:
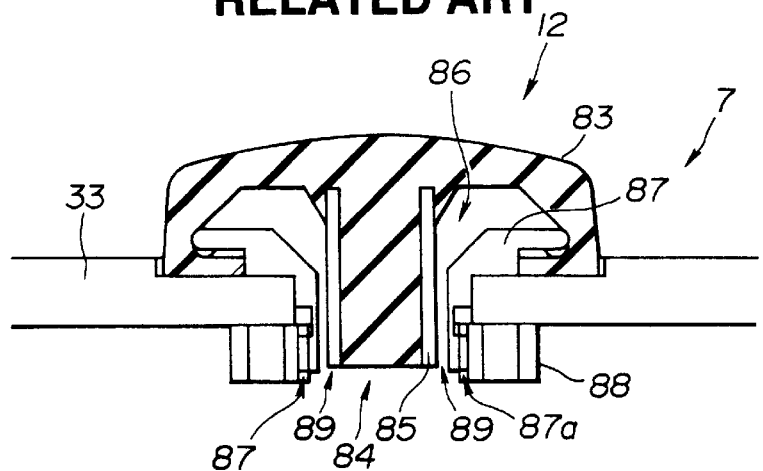
FIGS. 14 through 16 show the connection method of a switch section to the operation assembly.
Figure 15:
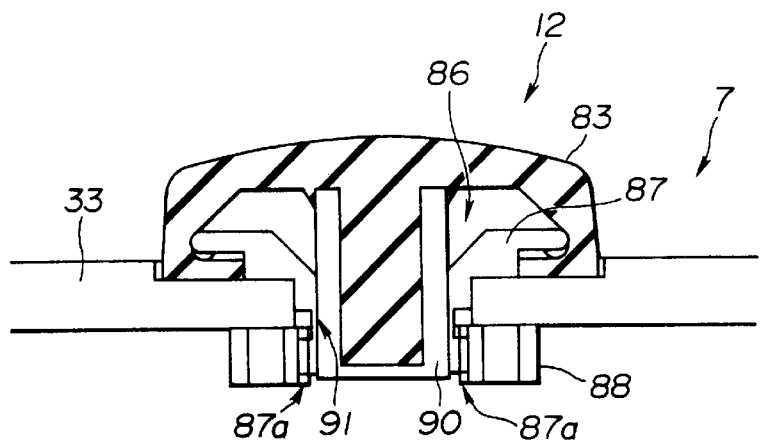
Figure 16:
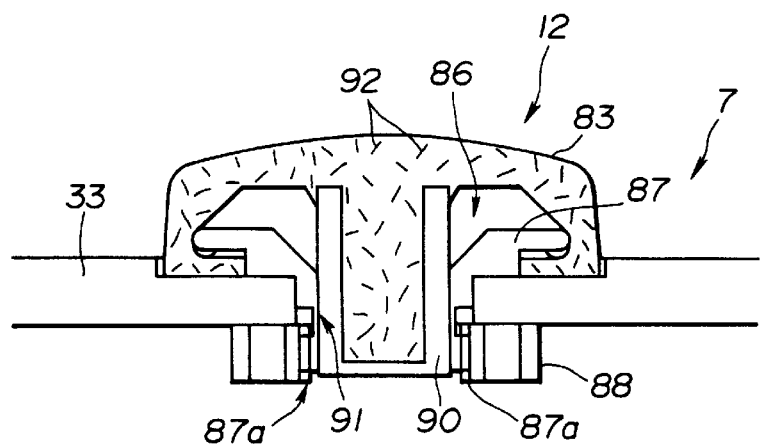

Discussed next referring to FIGS. 14 through 16 is the connection method of the switch section disposed in the operation assembly.

As shown in FIG. 14, a first support block 85 as a member to press an unshown control member located below the first opening 84 of a bushing 87 is embedded into the switch activating elastic member 83 disposed on the operation assembly 7 in the prior art electronic endoscope 3. It is difficult to integrally form the switch activating elastic member 83 and the operation assembly casing 33. To secure the switch activating elastic member 83 to the operation assembly casing 33, the metal bushing 87 is disposed in the space 86 formed inside the switch activating elastic member 83, and a fixing nut 88 is tightened around the threaded portion 87a formed on the bottom of the bushing 87, but a created gap 89 allows radiated noise to leak from inside through the gap 89 or noise to ingress from the outside.

For this reason, a second support block 90 is disposed as shown in FIG. 15 instead of the first support block 85 shown in FIG. 14. The second support block 90 that replaces the first support block 85 has a sliding face 91 that is in sliding engagement with the first opening 84 formed in the bushing 87. The rest of the construction remains unchanged from that in FIG. 14, and components equivalent to those with reference to FIG. 14 are designated with the same reference numerals, and the explanation on them will not be repeated.

By employing the structure that allows the second support block embedded into the switch activating elastic member to slide on the first opening of the bushing in this way, no gap results and a leak of radiated noise from within and noise ingress from outside are reduced.

As shown in FIG. 16, the switch activating elastic member 83 is manufactured by molding a resin that contains powdered noise absorbing material 92. Available as the powdered noise absorbing material 92 is the one having radio wave absorbing properties, such as carbon black, ferrite, acrylonitrile-copper sulfide composite fiber, carbonyl iron based material and the like. In this arrangement, radiated noise from within the operation assembly 7 and noise ingressing from outside the switching section 12 are absorbed by the powdered noise absorbing material 92. The rest of the construction, operation and advantage remains unchanged from that in FIG. 15.

Referring to FIGS. 17 through 26, the connection method is discussed which achieves firm electric connection in the front end portion of the insert assembly.

Figure 17:
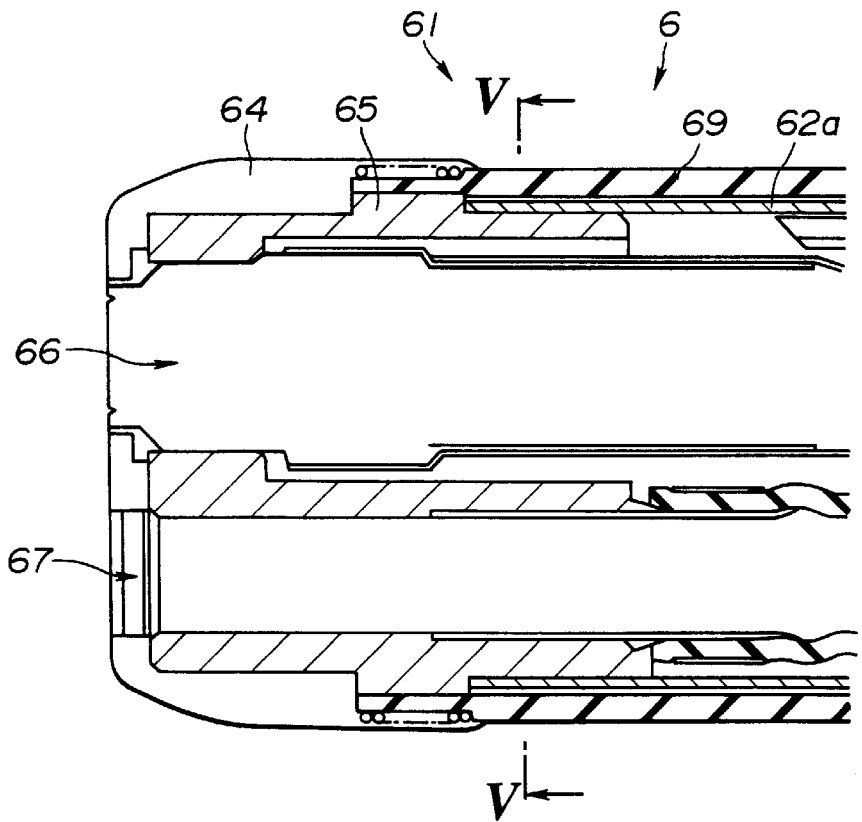
FIGS. 17 through 26 show the connection method of assuring electric continuity in the front end portion of the insert assembly.
Figure 18:
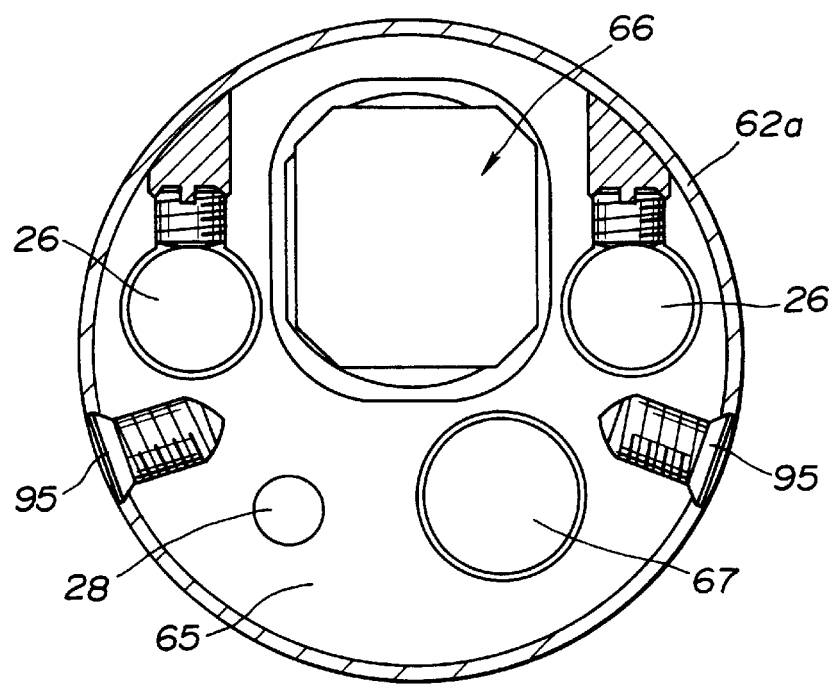

As shown in FIGS. 17 and 18, the front end portion 61 of the insert assembly 6 is constructed of a back block 65 on which an image pickup unit 66 and an instrument passage channel 67 are mounted and a front block 64 that protects the back block 65 and the front end of the image pickup unit 66. The first bending portion joint segment 62a that makes up the bending portion 62 is fitted into the back end of the back block 65 that forms part of the front end portion 61. The back end of the front end portion 61 and the outer circumference of the first bending portion joint segment 62a are covered with a bending portion covering member 69. Designated 95 are screws that secure the first bending portion joint segment 62a to the back block 65.

Figure 19:
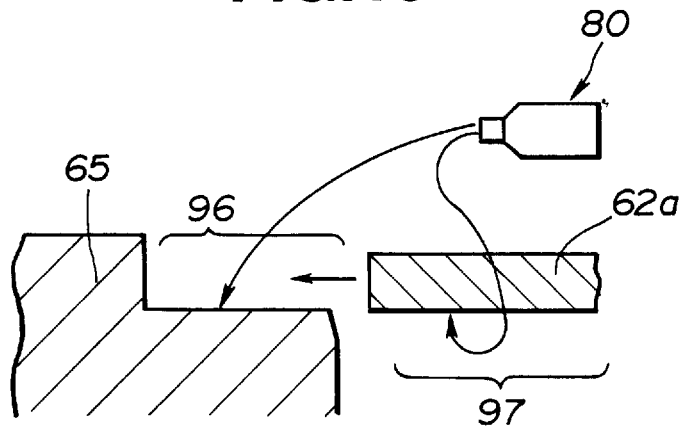

When the first bending portion joint segment 62a is connected to the back block 65 as shown in FIG. 19, the adequate quantity of a conductive adhesive 80 is applied to a mating face 96 to the first joint segment, of the back block 65 and a mating face 97 to the block, of the first bending portion joint segment 62a, and then both mating faces are engaged. If any gap should occur between the mating faces due to dimensional variations in diameter, the conductive adhesive 80 fills the gap, with its conductive material assuring electric continuity between the mating face 96 to the first joint segment, of the back block 65 and the mating face 97 to the block, of the first bending portion joint segment 62a.

Figure 20:
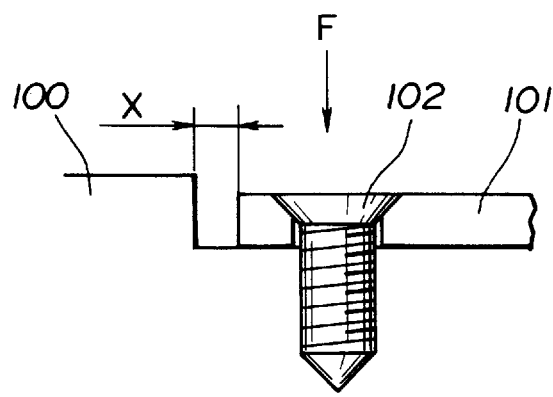
Figure 21:
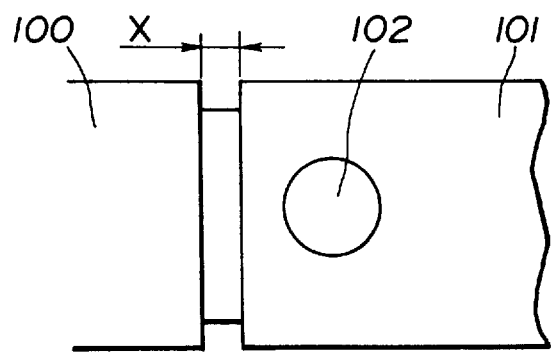
Figure 22:
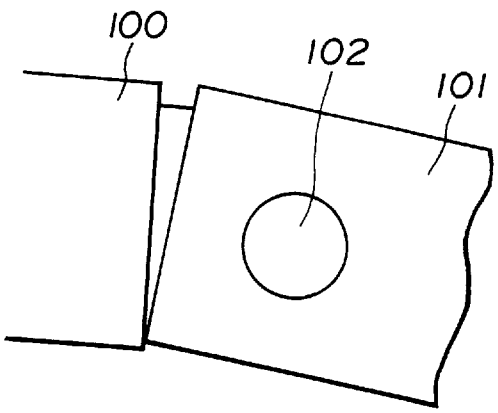

When electric continuity is assured by connecting members partly, particularly when electrically non-conductive members as a result of topcoating are connected for electric continuity, a step is disposed in one member. The topcoating of the wall portion of the step is peeled off by masking or other similar methods. The topcoating of the portion of the other member that faces the wall of the one member is peeled off, and both portions are arranged to abut each other. Screws at some distance away from the abutment portions are tightened to secure both members. In this case, to keep these wall portions abutted, the distance between the center line of the screw-head socket and the wall portion in one member and the distance between the center line of the screw hole and the wall portion in the other member are set to be equal. As shown in FIGS. 20 and 21, however, the positions of the center lines in the members 101, 102 suffer a variation depending on workmanship, possibly causing both members to fail to abut each other, with a gap x left therebetween, presenting difficulty establishing electric continuity or unstable connection therebetween as shown in FIG. 22. A structure is desired which offers both a reliable abutment with no gap x created and a reliable electric continuity.

Figure 23:
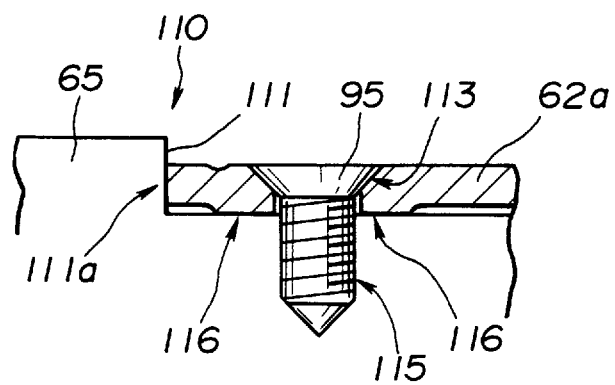

In this embodiment as shown in FIG. 23, the back block 65 is provided with a step 110 having a wall portion 111 to allow the end face of the first bending portion joint segment 62a to abut the back block 65. This embodiment thus forms a abutment portion 111a the end face of the first bending portion joint segment 62a abuts.

Figure 24:
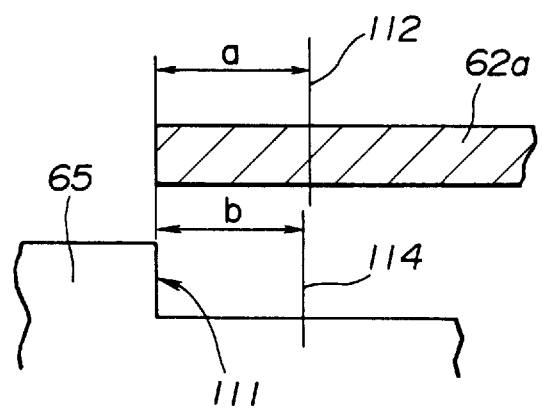
Figure 25:
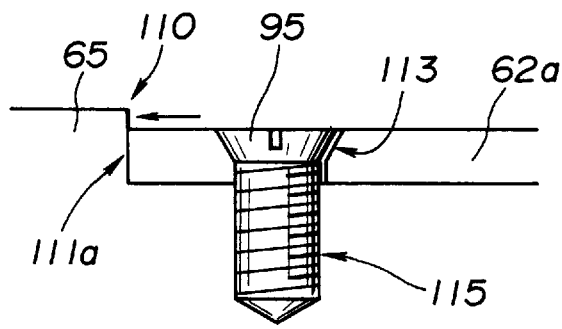

Next, as shown in FIG. 24, with respect to the wall portion 111 of the back block 65, a screw-head socket 113 is formed with its center line 112 spaced apart from the end face of the first bending portion joint segment 62a by the distance a, and a screw hole 115 is made with its center line 114 spaced apart by the distance b of the back block 65. In this case, the distances a and b hold the relationship of a>b, and the difference between a and b is set to be approximately equal to the height of the thread of the screw 95. As shown in FIG. 25, therefore, there is a positional discrepancy between the distances a and b, wherein the distance a is a separation between the center line 112 of the screw-head socket 113 and the wall portion 111 and the distance b is a separation between the center line 114 of the screw hole 115 and the wall portion 111.

To secure the back block 65 to the first bending portion joint segment 62a by tightening the screws 95, first the back block 65 is engaged with the first bending portion joint segment 62a, and the center line 112 of the screw-head socket and the center line 114 of the screw hole are roughly aligned. Next, the screw 95 is inserted through the screw-head socket 113 and then screwed into the screw hole 115 formed in the back block 65. Since the positional discrepancy takes place between the distance a to the center line 112 of the screwhead socket 113 and the distance b to the center line 114 of the screw hole 115, the first bending portion joint segment 62a is urged against the abutment portion 111a. When the screw 95 is fully tightened, the first bending portion joint segment 62a is firmly engaged with the abutment portion 111a, with no gap 1 and thus no looseness taking place, and reliable electric continuity is thus achieved. When the screw 95 is screwed, pressure arising from the meshing of the thread of the screw creates a contact area 116 as shown in FIG. 23 and electric continuity is thus established.

Figure 26:
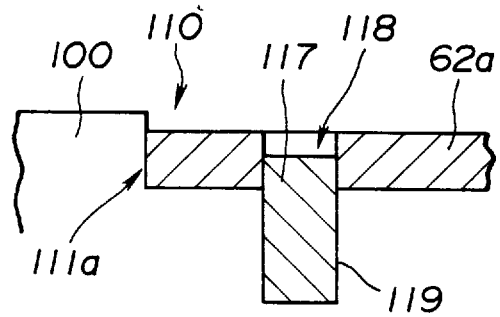

As shown in FIG. 26, the same operation and advantage will be achieved if the first bending portion joint segment 62a is secured to the back block 65 by a pin 117 rather than by the screw 95. In this case, a through-hole 118 and pin hole 119 into which the pin 117 is press-fitted are formed instead of the screw-head socket 113 and screw hole 115.

Discussed next referring to FIGS. 27 through 30 is the connection method that achieves firm electric connection in the instrument port ring.

Figure 27:
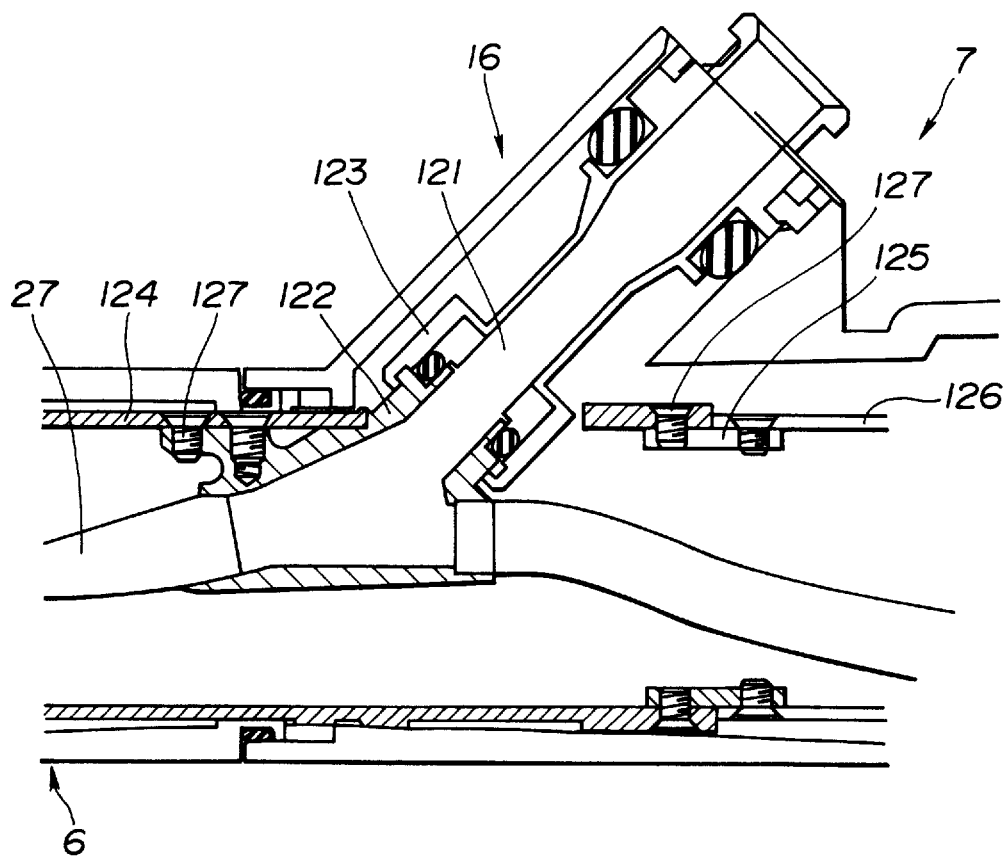
FIGS. 27 through 30 show the connection method of assuring electric continuity on the instrument port ring.

As shown in FIG. 27, the instrument port ring 16 has an instrument passage channel 121 that allows an unshown instrument to pass therethrough, and the instrument passage channel 121 communicates with the suction tube 27. The instrument that is inserted through the instrument port ring 16 then passes through the instrument passage channel 121 and the suction tube 27 in the insert assembly 6 and then is projected out of the front end portion 61.

The suction tube 27 is connected to the instrument passage channel 121 via a generally Y-shaped suction tube branching adapter 122, and the other port of the suction tube branching adapter 122 connects to the suction tube 27 that extends to the scope connector assembly 9. The instrument passage channel 121 is connected to the suction tube branching adapter 122 via an instrument port ring 123, which in turn is connected to the suction tube branching adapter 122. The suction tube branching adapter 122 is constructed of a conductive member, and is connected to a metal member 124 which has insulator coating. The insulator coated metal member 124 is attached via an operation assembly junction member 126 to a conductive member 125 disposed on the operation assembly 7. Screws 127 secure the metal member 124 to both the suction tube branching adapter 122 and the conductive member 125.

Figure 28:
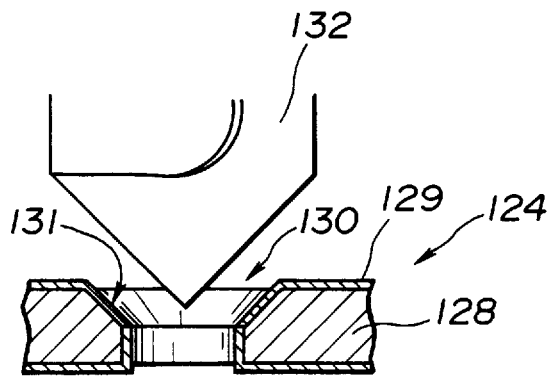

Discussed next referring to FIG. 28 is the method of assuring electric continuity of insulator coated metal members at the junction portion between the metal member 124 and the suction tube branching adapter 122 and at the junction portion between the metal member 124 and the conductive member 125.

Figure 29:
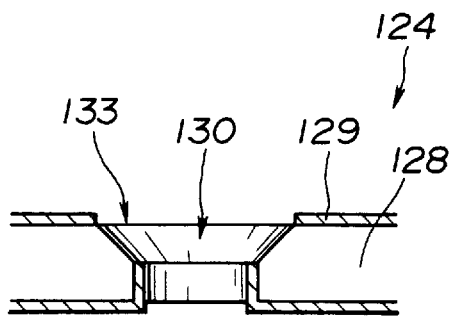

The metal member 124 is constructed by coating a conductive substrate 128 with an insulating film 129, and is provided with screw-head sockets 130 for the purpose of fixing. The wall 131 of the screw-head socket 130 is coated with the insulating film 129. To peel the insulating film 129 off the wall 131, a drill 132 is used to remove the insulating film 129. By using the drill 132 as shown in FIG. 29, an insulating-film free portion 133 is formed by removing the insulating film 129 off the wall 131 of the screw-head socket 130, and thus the substrate 128 that is generally covered with the insulating film 129 is partly exposed. Instead of using the drill to remove the insulating film, masking may be used to form the insulating-film free portion.

Figure 30:
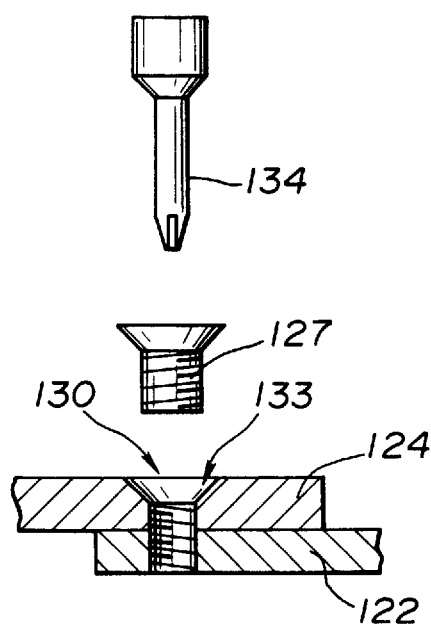

Next, as shown in FIG. 30, using a torque driver 134, screws 27 are tightened with the screw-head sockets 130 of the metal member 124 having the insulating-film free portions 133 aligned with the screw hole of the suction tube branching adapter 122 and the screw hole of the conductive member 125. In this case, a driving torque of 3 kgf·cm is appropriate, and this level of driving torque is expected to firmly tighten the screws while providing reliable electric continuity. This level of torque is applicable to other points where both mechanical fixing and electric continuity have to be established in the endoscope.

As described above, by peeling off the insulating film and tightening the screws at a proper torque, a reliable mechanical fixing and reliable electric continuity result.

Figure 31:
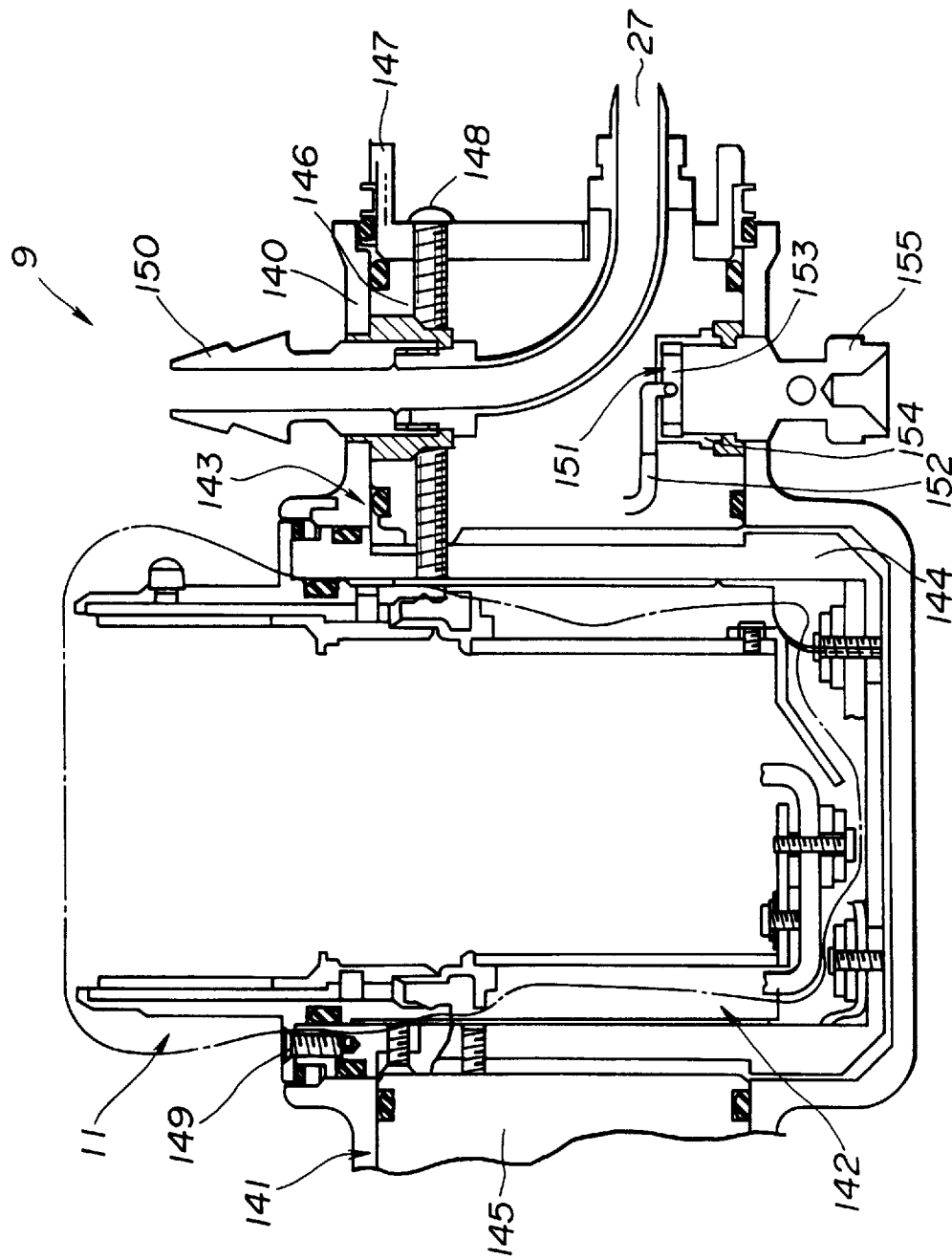
FIG. 31 shows the connection method that assures electric continuity of a scope connector assembly.

Referring to FIG. 31, discussed finally is the connection method of providing firm electric continuity in the scope connector assembly.

As shown, the resin connector case 140 of the scope connector assembly 9 is provided with a first opening 141, a second opening 142, and a third opening 143. A base 144 is fitted into the second opening 142, and a first block 145 and a second block 146 are fitted into the first and third openings 141, 143, respectively. Both the first block 145 and second block 146 are kept in firm contact with the base 144.

The second block 146 fitted into the third opening 143 is pressed tightly to and secured to the base 144 via a lid 147 by tightening a conductive screw 148. The connector case 140 is free from stress arising from tightening action of the conductive screw 148. The base 144, the conductive screw 148 and the lid 147 are constructed of conductive materials. The same connection method and material are employed for the opposite first opening 141.

The electric connector 11 is fitted into the second opening 142 and secured to the base 144 with fixing screws 149. Embedded in the second block 146 is the suction tube adapter 150 for connecting the suction tube 27 to an external tank. To avoid any hazard to a patient arising from leakage current flowing into the patient during high-frequency treatment, a terminal socket 151 is formed so that a clamp 154 and a terminal 153 are pressed into contact with the terminal 153 connected to a ground line 152 contained in the universal cord 8. The terminal 155, the ground line 152, the terminal 153 and the clamp 154 are made of conductive materials. The second block 146 is made of a non-conductive material, for example, a molded component. When a high-frequency treatment is performed, leakage currents from the operation assembly 7 and the insert assembly 6 are designed to be grounded externally via the ground line 152 and the terminal 155 to assure the safety of a patient, and for this reason, the second block 146 should be non-conductive. Since this is non-conductive, the lid 147 is electrically connected to the base 144 via the conductive screw 148.

As described above, when non-conductive members are interposed, electric continuity is provided by using conductive fixing members.

It should be understood that various embodiments of the present invention may be effected in a wide range without departing from the spirit and scope of the present invention. Therefore, the present invention should be limited to the appended claims rather than to the specific embodiments disclosed herein.

What is claimed is:

1. An endoscopic apparatus comprising:
   a solid-state image pickup device installed in an insert assembly;
   a signal transmission member for conducting an electric signal into which said solid-state image pickup device photoelectrically converts an optical image;
   any one of a flexible tube-like metal member that makes up part of a cover of said insert assembly, a flexible tube-like metal member that makes up part of an universal cord assembly, and both said insert assembly cover flexible tube-like metal member and said universal cord cover flexible tube-like metal member, whereby said signal transmission member is inserted through said insert assembly and said universal cord assembly;
   a shield member that covers said signal transmission member is disposed in any one of at least a part of said insert assembly, a part of said universal cord assembly, and both said part of said insert assembly and said part of said universal cord assembly and said shield member has an electrically conductive connection with said insert assembly cover and said universal cord assembly cover flexible tube-like metal members; and
   an operation assembly having a casing with an inner surface, wherein at least in said operation assembly, an operation assembly cover metal member that forms an operation assembly support plate, an angle shaft mounted on said operation assembly support plate, and a conductive coating disposed in said inner surface of said casing of said operation assembly are put into contact via a connection member, wherein said shield member is electrically conductively connected to at least one of said operation assembly support plate, said angle shaft and said conductive coating.

2. The endoscopic apparatus according to claim 1, wherein said signal transmission member is a signal cable comprising a plurality of signal lines in a bundle and each of said signal lines is shielded by first shields, while a second shield covers said signal cable made up of said plurality of said signal lines in said bundle.

3. The endoscopic apparatus according to claim 2, further comprising circuit grounds to which said first shields and said second shield are electrically connected.

4. The endoscopic apparatus according to any one of claims 2 and 3, wherein said shield member is isolated from said plurality of signal lines, said first shields and said second shield.

5. The endoscopic apparatus according to claim 1, wherein said shield member is constructed of a metal braided shield having a density of 50% or more.

6. The endoscopic apparatus according to claim 1, wherein said shield member that covers said signal transmission member, is electrically conductively connected to said operation assembly cover metal member.

7. The endoscopic apparatus according to claim 1, wherein said shield member and said insert assembly cover and said universal cord assembly cover flexible tube-like metal members are disposed in any one of a close vicinity to each other and in contact with each other and are electrically conductively connected to each other.

8. The endoscopic apparatus according to claim 7, wherein said connection member is an elastic member supported by said operation assembly support plate.

9. The endoscopic apparatus according to claim 1, wherein in said operation assembly, said signal cable and said operation assembly support plate are electrically connected to each other via a jumper wire.

10. The endoscopic apparatus according to claim 1, wherein a bottom surface of said operation assembly support plate and a top surface of a flange portion of said angle shaft are put into contact and connected with a screw.

11. The endoscopic apparatus according to claim 10, wherein said screw that connects said top portion of said flange portion of said angle shaft to said operation assembly support plate is coated with a conductive adhesive.

12. The endoscopic apparatus according to claim 1, wherein said operation assembly support plate of said operation assembly and a cylinder that makes up an air/water feed control section are electrically connected via jumper wires.

13. The endoscopic apparatus according to claim 1, wherein a switch activating elastic member in said operation assembly is provided with a support block that is in slidable engagement with an opening formed in a bushing.

14. The endoscopic apparatus according to claim 13, wherein a resin material that constructs said switch activating elastic member contains a powdered noise absorbing material.

15. The endoscopic apparatus according to claim 7 further comprising:
   a bending portion having a plurality of joint segments consecutively linked in said insert assembly;
   an angle wire for manipulating said bending portion for curving operation; and
   an angle coil pipe made of a conductive material for allowing said angle wire to pass therethrough, whereby said signal transmission member extends through said angle coil pipe.

16. The endoscopic apparatus according to claim 15, wherein a conductive adhesive is applied in a gap between a back block and a joint segment of said plurality of joint segments when said back block that makes up a front end portion of said insert assembly is connected to said joint segment of said plurality of joint segments that makes up an end of said bending portion.

17. The endoscopic apparatus according to any one of claims 2 and 15, wherein said signal cable is coiled into a cable loop in said operation assembly.

18. The endoscopic apparatus according to claim 1, further comprising a first member having a step and an engagement hole, wherein said engagement hole of said first member is roughly aligned with a through-hole of a second member, said second member being a part of said flexible tube-like metal member which makes up a part of said cover of said insert assembly and an abutment portion that abuts a step of said first member, whereby a distance between said step and a center line of said engagement hole on said first member is set to be shorter than a distance between said abutment portion and said center line of said through-hole when said first member is connected to said second member.

19. The endoscopic apparatus according to claim 1, further comprising a first conductive metal member which is connectable to a second metal member, said second metal member being a part of said flexible tube-like metal member which makes up a part of said cover of said insert assembly and said second metal member being made of a conductive substrate having an insulating coating, whereby an insulating coating free portion is provided by peeling said insulating coating off said second metal member when said first metal member is connected to said second metal member.

20. The endoscopic apparatus according to claim 1, further comprising an insulator member between said insert assembly cover and said universal cord assembly cover flexible tube-like metal members, whereby said insert assembly cover and said universal cord assembly cover flexible tube-like metal members are connected with a conductive screw.

21. An endoscopic apparatus comprising:
   a solid-state image pickup device installed in an insert assembly;
   a signal transmission member for conducting an electric signal into which said solid-state image pickup device photoelectrically converts an optical image;
   any one of a flexible tube-like metal member that makes up part of a cover of said insert assembly, a flexible tube-like metal member that makes up part of an universal cord assembly, and both said insert assembly cover flexible tube-like metal member and said universal cord assembly cover flexible tube-like metal member, whereby said signal transmission member is inserted through said insert assembly and said universal cord assembly;
   a shield member that covers said signal transmission member is disposed in any one of at least a part of said insert assembly, a part of said universal cord assembly, and both a part of said insert assembly and a part of said universal cord assembly and said shield member has an electrically conductive connection with said insert assembly cover and said universal cord assembly cover flexible tube-like metal members, wherein said shield member, said insert assembly cover and said universal cord assembly cover flexible tube-like metal members are disposed in any one of a close vicinity to each other and in contact with each other and are electrically conductively connected to each other;
   a bending portion having a plurality of joint segments consecutively linked in said insert assembly;
   an angle wire for manipulating said bending portion for curving operation; and
   an angle coil pipe made of a conductive material for allowing said angle wire to pass therethrough, whereby said signal transmission member extends through said angle coil pipe.

* * * * *